(12) United States Patent
Lunn et al.

(10) Patent No.: US 9,687,224 B2
(45) Date of Patent: Jun. 27, 2017

(54) ANCHOR ASSEMBLY

(71) Applicant: Smith & Nephew, Inc., Memphis, TN (US)

(72) Inventors: Richard M. Lunn, Kingston, MA (US); David A. Paulk, Hopedale, MA (US); Thomas C. May, Wrentham, MA (US); Steven W. Astorino, Norfolk, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/969,229

(22) Filed: Dec. 15, 2015

(65) Prior Publication Data

US 2016/0100833 A1    Apr. 14, 2016

Related U.S. Application Data

(62) Division of application No. 12/259,106, filed on Oct. 27, 2008, now Pat. No. 9,345,467.

(60) Provisional application No. 60/986,342, filed on Nov. 8, 2007, provisional application No. 60/982,521, filed on Oct. 25, 2007.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0403* (2013.01); *A61B 2017/044* (2013.01); *A61B 2017/0409* (2013.01); *A61B 2017/0412* (2013.01); *A61B 2017/0414* (2013.01); *A61B 2017/0427* (2013.01); *A61B 2017/0445* (2013.01); *A61B 2017/0453* (2013.01); *A61F 2002/0829* (2013.01); *A61F 2002/0888* (2013.01)

(58) Field of Classification Search
CPC .... A61B 2017/0414; A61B 2017/0412; A61B 2017/0427; A61B 17/0401
See application file for complete search history.

(56) References Cited

U.S. PATENT DOCUMENTS

| | | | | |
|---|---|---|---|---|
| 2006/0004364 | A1* | 1/2006 | Green | A61B 17/0401 606/232 |
| 2007/0203498 | A1* | 8/2007 | Gerber | A61B 17/0401 606/328 |
| 2007/0288023 | A1* | 12/2007 | Pellegrino | A61B 17/0401 606/232 |

* cited by examiner

Primary Examiner — David Bates
(74) Attorney, Agent, or Firm — Norman F. Hainer, Jr.

(57) ABSTRACT

The present disclosure relates to an anchor assembly. The anchor assembly includes an anchor defining a cavity and an opening to the cavity and an insertion member configured for arrangement within the anchor cavity. The insertion member includes a body having a proximal end portion and a flat distal end portion, and a head coupled to the proximal end portion of the body. A method of tissue repair and other anchor assemblies are also disclosed.

5 Claims, 7 Drawing Sheets

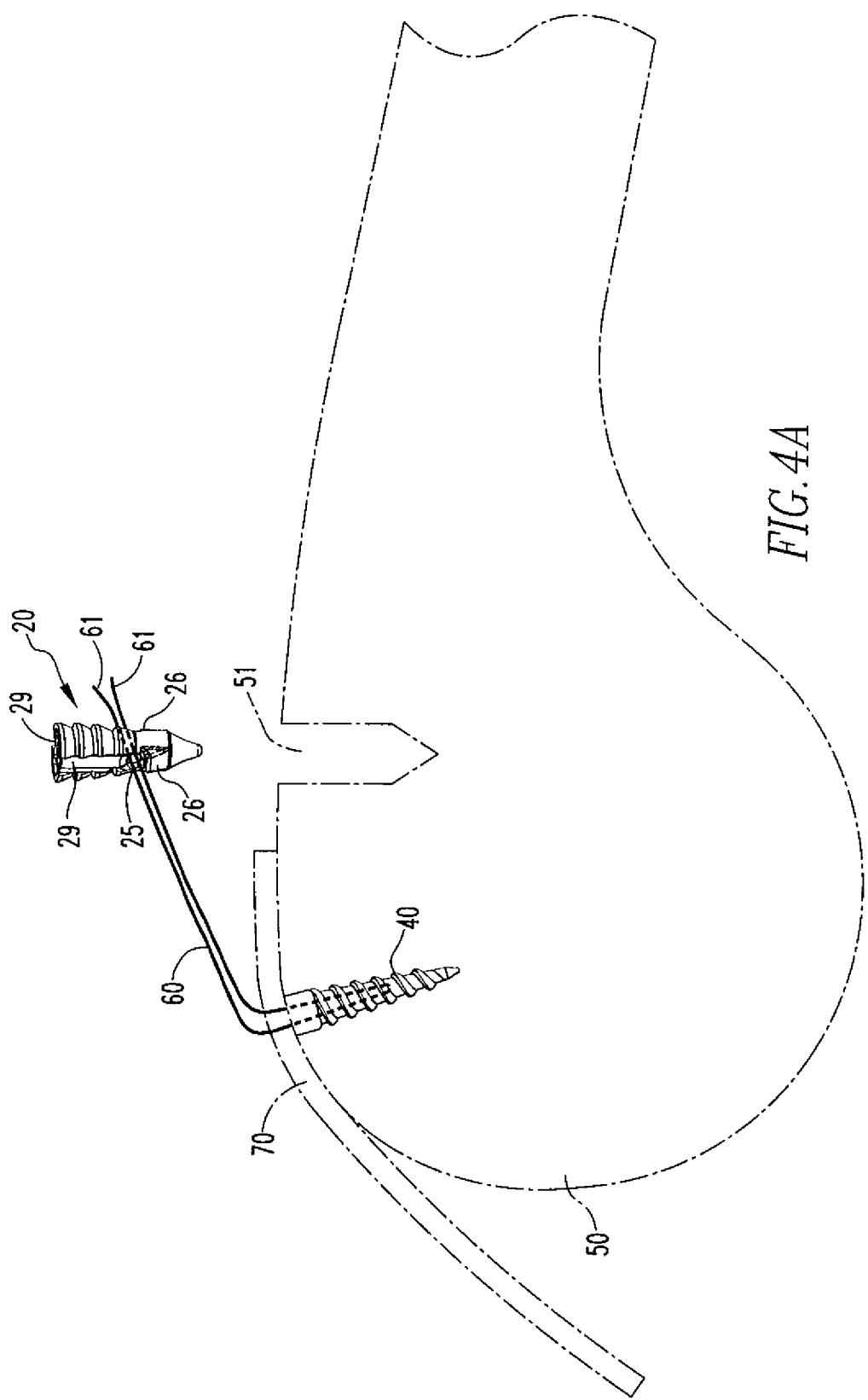

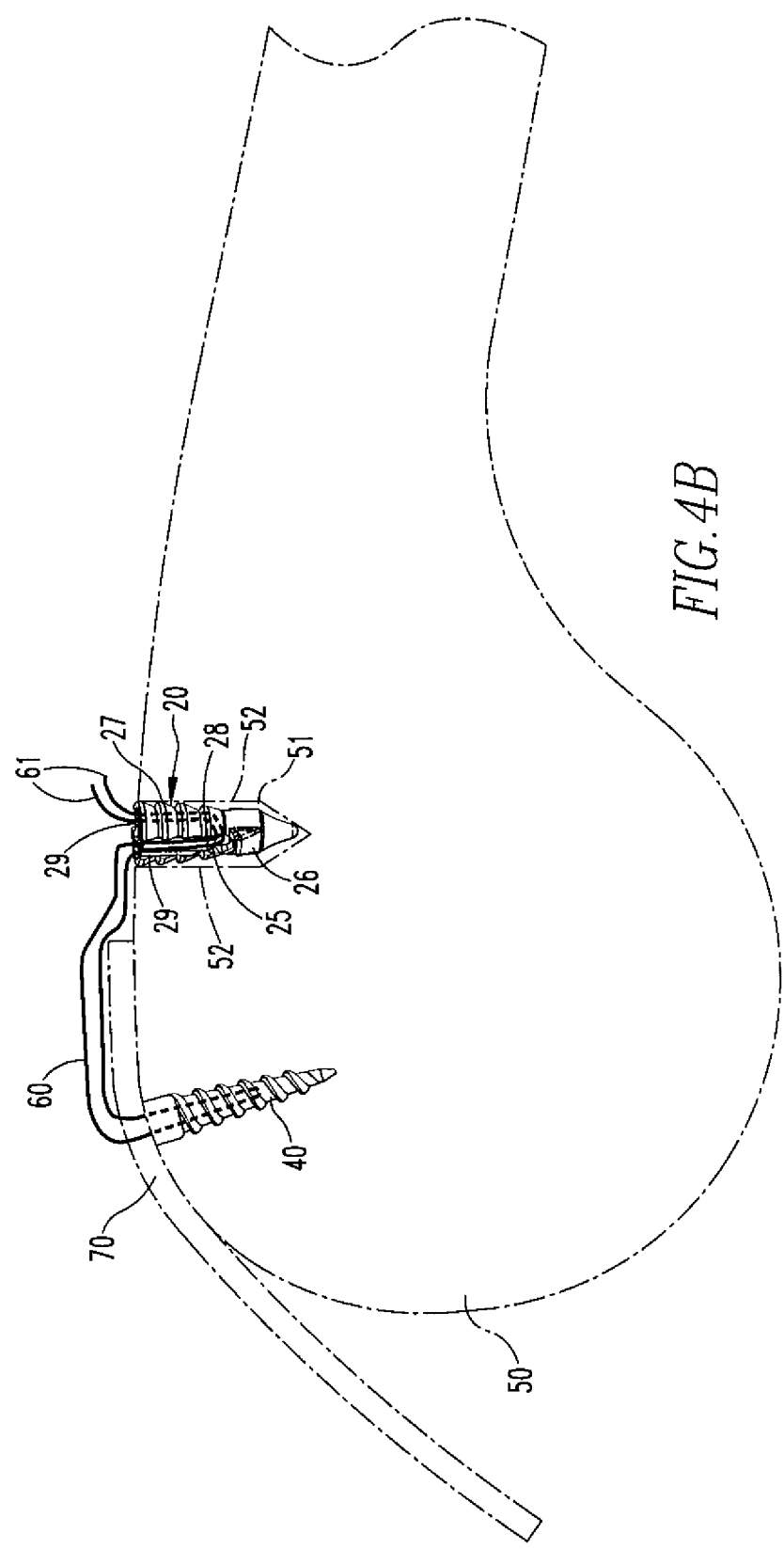

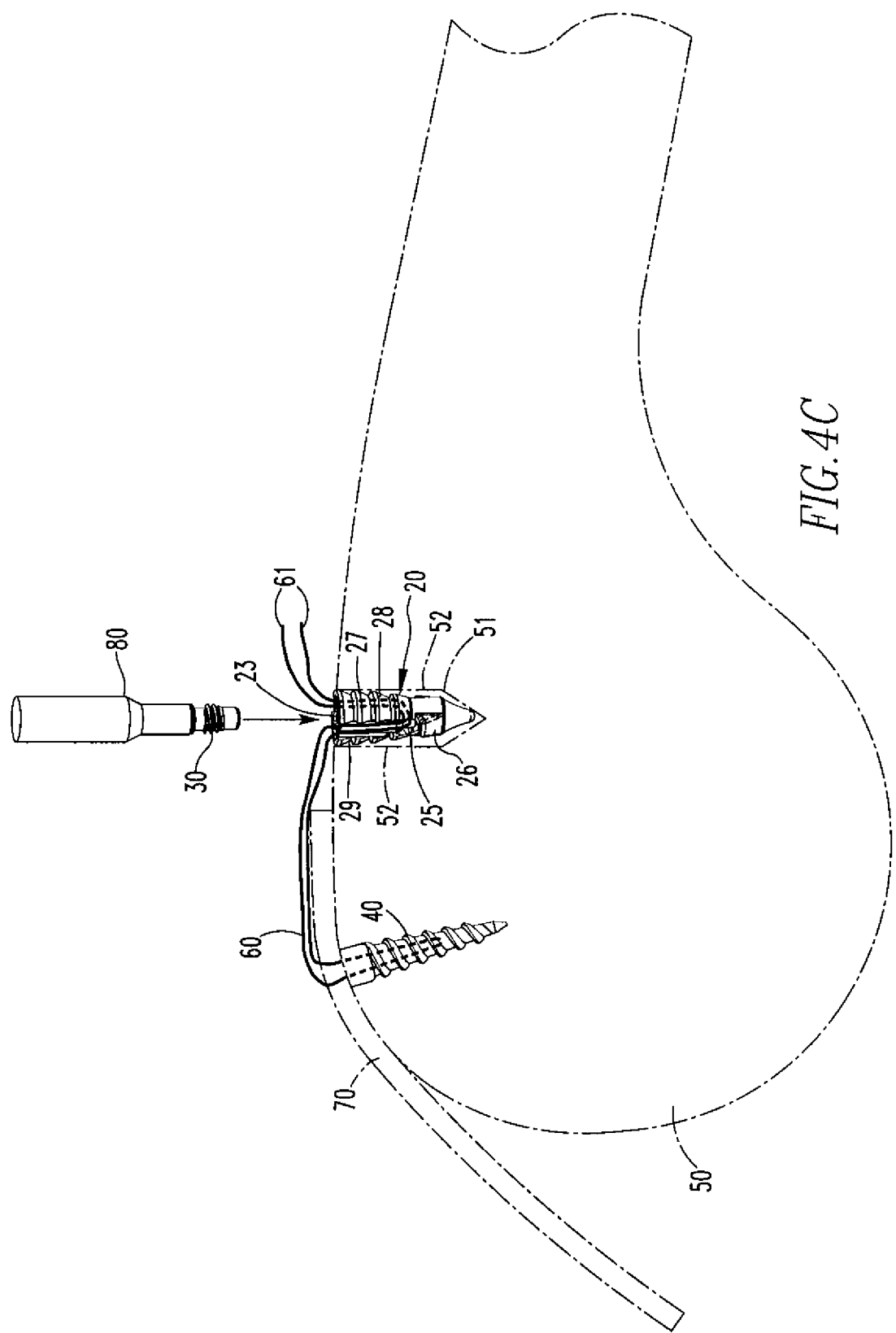

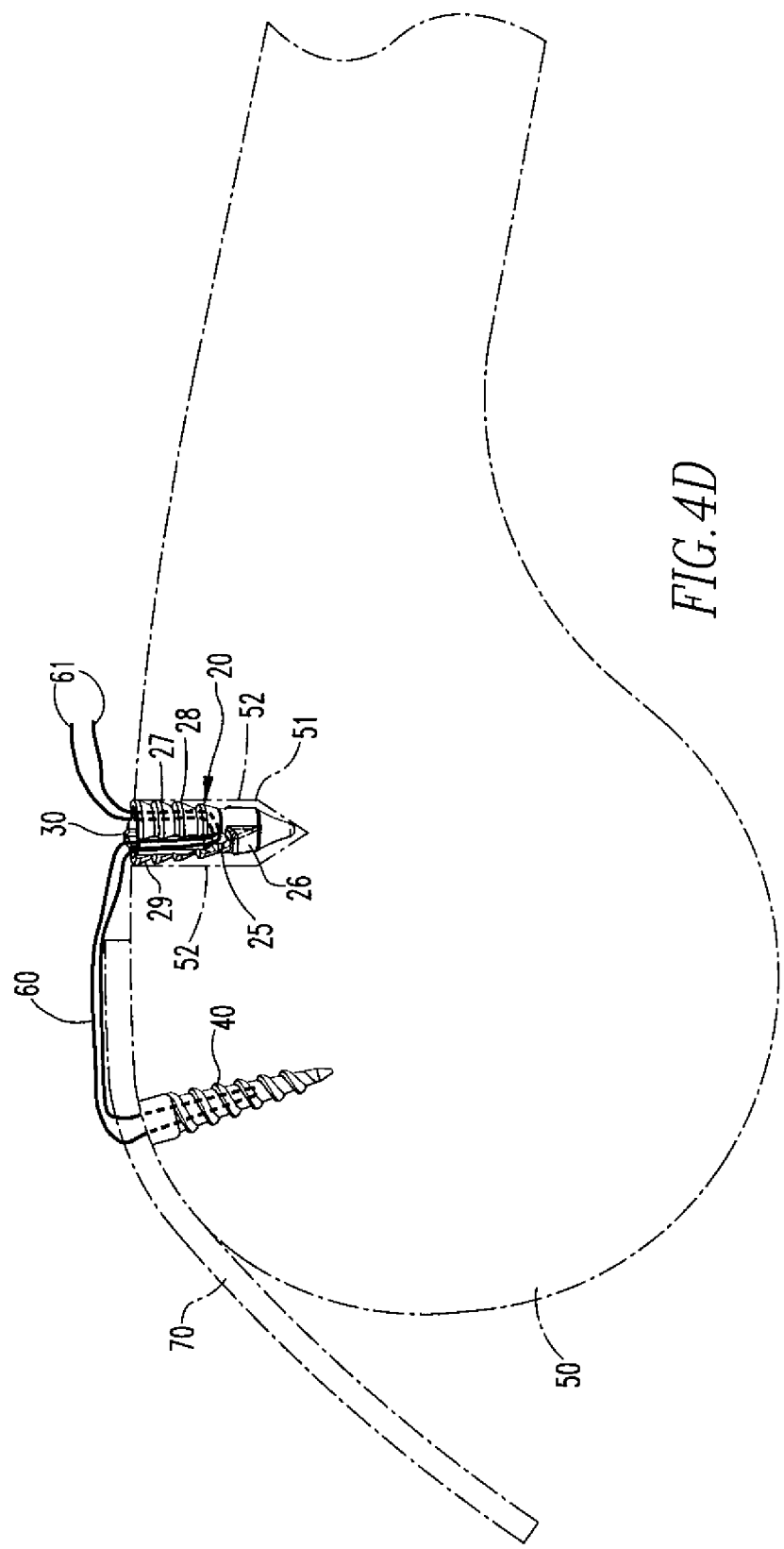

ANCHOR ASSEMBLY

CROSS-REFERENCE TO RELATED APPLICATIONS

This application is a divisional of pending U.S. application Ser. No. 12/259,106, filed Oct. 27, 2008, which claimed the benefit of U.S. Provisional Application No. 60/986,342, filed Nov. 8, 2007 and U.S. Provisional Application No. 60/982,521, filed Oct. 25, 2007. The disclosure of each application is incorporated herein by reference in their entireties.

BACKGROUND

Field of Technology

The present disclosure relates to tissue repair, and more specifically, to an anchor assembly for securing tissue to bone.

Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

SUMMARY

In one aspect, the present disclosure relates to an anchor assembly. The anchor assembly includes an anchor defining a cavity and an opening to the cavity and an insertion member configured for arrangement within the anchor cavity. The insertion member includes a body having a proximal end portion and a flat distal end portion, and a head coupled to the proximal end portion of the body. The anchor includes protrusions located on an outer surface of the anchor, wherein the protrusions are configured to facilitate loading of a flexible member into the anchor. In an embodiment, the anchor assembly further includes a transverse through hole extending through the anchor. In another embodiment, the anchor assembly further includes at least two slots on an outer surface of the anchor, wherein the slots extend from the transverse through hole to a proximal portion of the anchor. In yet another embodiment, the anchor includes barbs on an outer surface of the body, wherein the barbs are intersected by the slots.

In a further embodiment, at least one flexible member, which may be a suture, is disposed within the through hole. In yet a further embodiment, a plurality of flexible members are disposed within the through hole. In yet an even further embodiment, the cavity includes threads. In an embodiment, the insertion member body includes threads, wherein the threads are configured for engagement with the threads of the cavity when the insertion member is arranged within the cavity. In another embodiment, the cavity extends into the through hole. In yet another embodiment, the head is configured for engagement with a delivery device. In a further embodiment, the insertion member is arranged within the anchor cavity such that the insertion member secures the flexible member in the through hole.

In another aspect, the present disclosure relates to a method of tissue repair. The method includes inserting a first anchor into bone, the first anchor having a flexible member coupled thereto; passing ends of the flexible member through the tissue; providing a second anchor defining a cavity and an opening to the cavity and a transverse through hole extending through the anchor; passing at least one end of the flexible member through the through hole of the second anchor; placing the second anchor into bone; providing an insertion member including a body having a proximal end portion and a flat distal end portion, and a head coupled to the proximal end portion of the body; and placing the insertion member within the anchor cavity of the second anchor to secure the flexible member in the through hole and the tissue to the bone.

In an embodiment, the method further includes tensioning the flexible member before placing the insertion member within the anchor cavity. In another embodiment, the method further includes moving the insertion member away from the through hole, tensioning the flexible member, and moving the insertion member back toward the through hole to resecure the flexible member in the through hole. In yet another embodiment, the second anchor includes protrusions, wherein the protrusions create paths in a wall of the bone when the second anchor is inserted into the bone. The paths allow the flexible member to slide through the second anchor when the second anchor is located in the bone.

In yet another aspect, the present disclosure relates to an anchor assembly. The anchor assembly includes an anchor defining a proximal portion, a distal portion, and an inner cavity; and an insertion member configured for arrangement within the inner cavity. The anchor includes barbs located on the proximal portion and protrusions located on the distal portion, wherein the protrusions are configured to facilitate loading of a flexible member into the anchor. In an embodiment, the insertion member includes a proximal end portion and a flat distal end portion.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 4A-4D show use of the anchor assembly of the present disclosure in repairing tissue.

DETAILED DESCRIPTION OF THE EMBODIMENTS

The following description of the preferred embodiment(s) is merely exemplary in nature and is in no way intended to limit the disclosure, its application, or uses.

Figure 1:
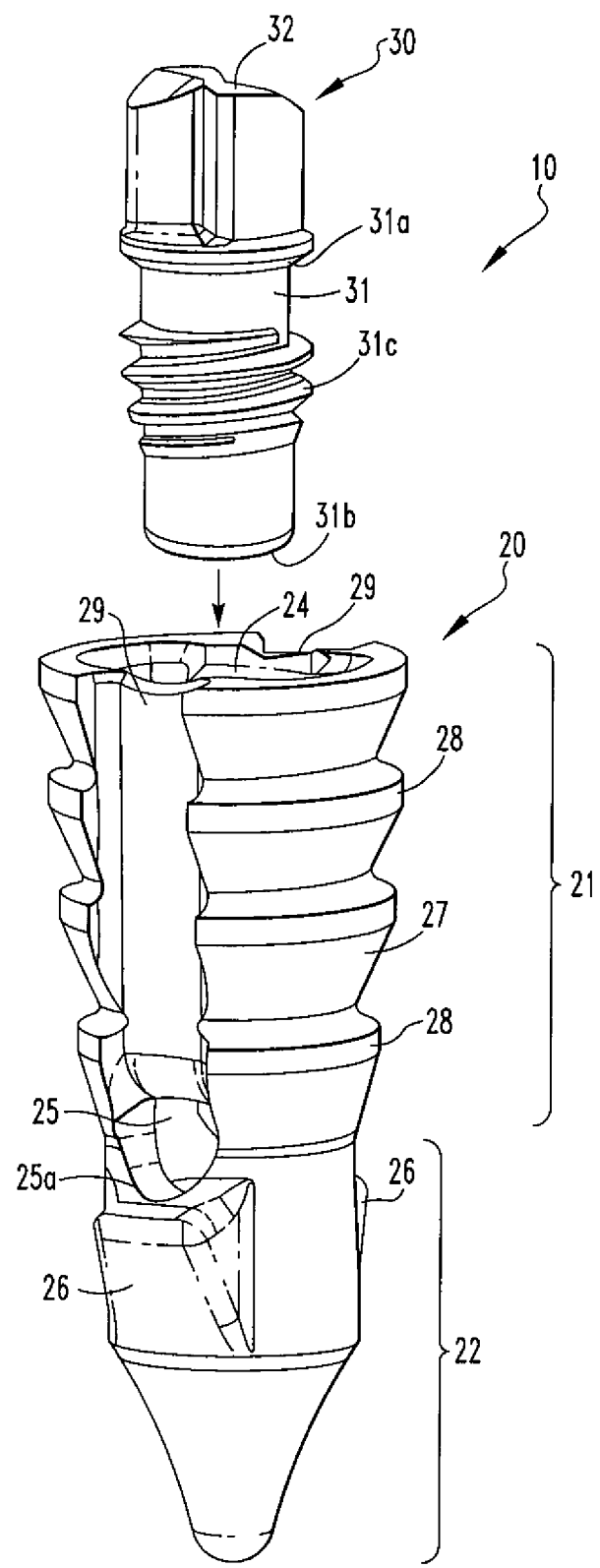
FIG. 1 shows an exploded view of the anchor assembly of the present disclosure.
Figure 2:
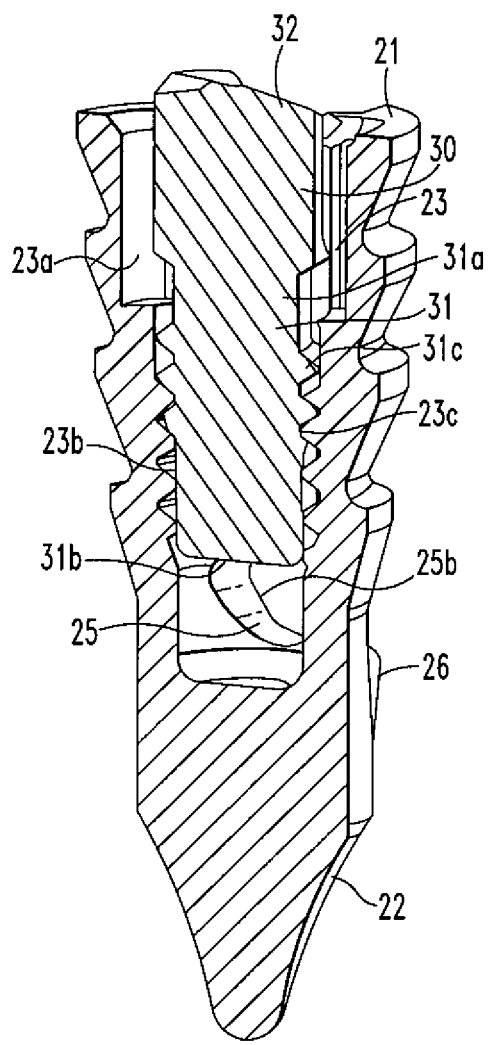
FIG. 2 shows a cross-sectional view of the anchor assembly of the present disclosure.
Figure 3:
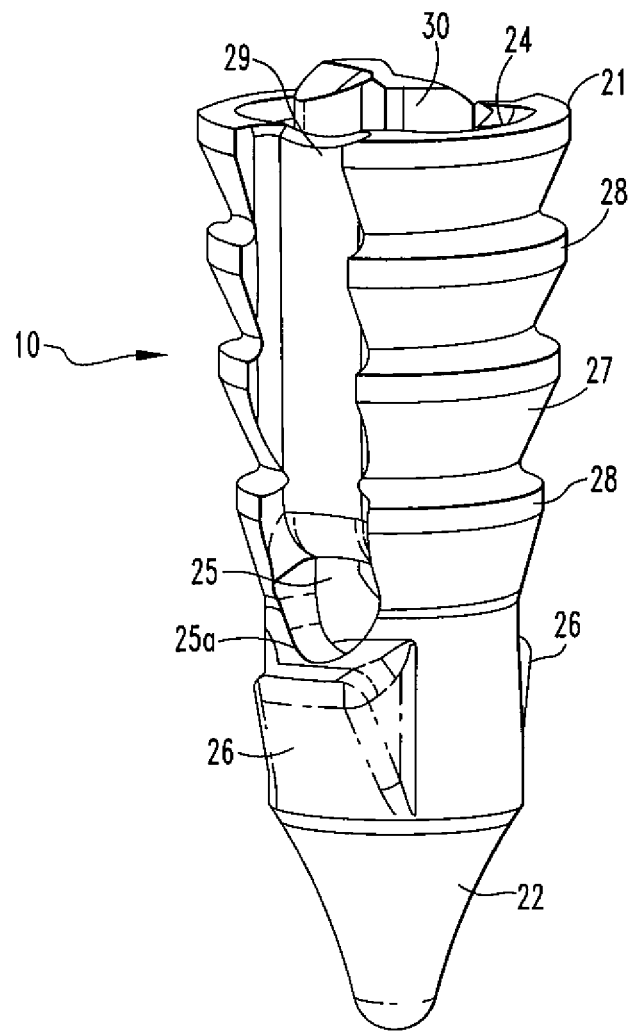
FIG. 3 shows a front view of the anchor assembly of the present disclosure.

FIGS. 1-3 show the anchor assembly 10 of the present disclosure. The assembly 10 includes the anchor 20 and the insertion member 30. The anchor 20 includes a proximal portion 21, a distal portion 22, and an inner cavity 23. An opening 24 to the cavity 23 is located at the proximal portion 21 of the anchor 20. A transverse through hole 25 is located between the proximal and distal portions 21,22 and extends through the anchor 20. Openings 25a,b are located at each end of the through hole 25. Located below each opening 25a,b is a protrusion 26. The protrusions 26 facilitate loading of a flexible member, such as a suture, through the through hole 25, and allow for the creation of a path in the wall of a bone hole when the anchor 20 is inserted into bone hole, as will be further described below. The outer surface 27 of the proximal portion 21 also includes barbs 28 for substantially reducing the possibility of removal of the anchor 20 when inserted into bone, as will be further described below. The outer surface 27 also includes slots 29 extending from the openings 25a,b of the through hole 25 to the proximal portion 21 of the anchor 20. The slots 29 intersect the barbs 28 and are configured for housing of the suture after positioning of the anchor 20 in bone, as further described below. As shown in FIG. 2, the cavity 23 extends into the through hole 25 and includes a proximal portion 23a and a threaded distal portion 23b for receipt of the insertion member 30, as will be further described below.

The insertion member 30 includes a body 31, having a proximal end portion 31a and a flat distal end portion 31b, and a head 32 coupled to the proximal end portion 31a. The head 32 is configured for engagement with a delivery tool and the body 31 includes threads 31c that are configured for engagement with the threads 23c of the cavity 23 when the insertion member is arranged within the cavity 23, as shown in FIG. 2.

The anchor 10 of the present disclosure may be used in conjunction with another anchor to repair soft tissue. FIGS. 4A-4D show the anchor assembly 10 in use during arthroscopic repair of the rotator cuff. However, the anchor assembly 10 may be used in the repair of soft tissue in other parts of the body. FIG. 4A shows a first anchor 40 that has been inserted into the lateral aspect of a bone 50, such as a humeral bone. The anchor 40, which has a flexible member 60, such as a suture, coupled thereto is inserted into the bone 50, a soft tissue 70, such as a rotator cuff tendon, is placed on the bone 50 to be located adjacent to the anchor 40, and the ends 61 of the flexible member 60 are placed through the soft tissue 70.

Next, at least one end 61 of the flexible member 60 is passed through the transverse through hole 25 of a second anchor, such as the anchor 20 of the present disclosure, and the anchor 20 is subsequently placed into a previously drilled hole 51 in the medial aspect of the bone 50, as shown in FIG. 4B, such that the flexible member 60 is housed within the transverse through hole 25 and both slots 29 of the anchor 20 and the ends 61 extend out of the hole 51. The anchor 20 is advanced into the hole 50 in an axially-oriented manner by tapping on the end of a delivery tool (not shown) that is used to deliver the anchor 20 into the hole 51. FIGS. 4B-4D show spaces between the outer surface 27 of the anchor 20 and the walls 52 of the hole 51. However, the diameter of the hole 51 will be sized such that the barbs 28 of the anchor 20 will abut the walls 52, and most likely extend through the walls 52 and into the bone 50, in order to substantially reduce the possibility of anchor removal. In addition, due to the hole diameter, the protrusions 26 located below the openings 25a,b create a path (not shown) in the wall of the bone hole 51 when the anchor 20 is inserted into hole 51. This path allows the suture 60 to slide when through the anchor 20 when the anchor 20 is located within the hole 51.

After placement of the anchor 20 into the hole 51, the ends 61 of the flexible member 60 may be pulled to provide a preferred amount of tension on the flexible member 60 and the soft tissue 70. This tension on the flexible member 60 can be seen in FIGS. 4C-D, especially when comparing these figures to FIG. 4B. The insertion member 30 is subsequently placed in the anchor cavity 23 in a rotary manner, via a delivery tool 80, to secure the flexible member 60 in the through hole 25 and the tissue 70 to the bone 50. The insertion member 30 may be removed from the cavity 23 to re-tension the flexible member 60 and then replaced within the cavity 23 to re-secure the flexible member 60 in the through hole 25.

The components of the anchor assembly 10 and the first anchor 40 are made from a bioabsorbable polymer material via an injection molding process. However, other materials and processes may be used. In addition, the suture material is made from a bioabsorbable polymer material, but other material may be used. Also, the initial anchor, such as the first anchor 40 shown above, may include more than one suture and the sutures may be secured together at one attachment point, such as within the second anchor 20 shown above, or independently at more than one attachment point. Furthermore, the outer surface 27 of the anchor 20 may include features other than barbs 28 to reduce the possibility of removal of the anchor 20 and the barbs 28 may extend the entire length or a partial length of the anchor 20. Similarly, the body 31 of the insertion member 30 and the cavity 23 of the anchor 20 may include features other than threads to facilitate insertion and removal of the insertion member 30 and the threads may extend the entire length or a partial length of the body 31 and cavity 23. Also, for the purposes of this disclosure, the through hole 25 is located between the proximal 21 and distal 22 portions, but may be located anywhere along the length of the anchor 20.

The anchor assembly 10 of the present disclosure allows a surgeon to load a suture from a previously placed anchor and secure the suture in the assembly 10 at a preferred tension. In addition, the assembly 10 allows the tension on the suture to be adjusted with tactile feedback. Furthermore, the assembly allows for one or more sutures to be secured together at one attachment point, such as described above with the second anchor 20, or independently at several attachment points. This allows for a large area of contact between the tissue and the bone and results in a better repair.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:
1. A method of tissue repairing tissue comprising:
 inserting a first anchor into bone, the first anchor having a flexible member coupled thereto;
 passing ends of the flexible member through the tissue;
 passing at least one end of the flexible member through a transverse through hole extending through a second anchor, the second anchor further defining an anchor cavity and an opening to the anchor cavity;

placing the second anchor into the bone; and placing an insertion member within the anchor cavity of the second anchor to secure the flexible member in the through hole and the tissue to the bone, the insertion member including a body having a proximal end portion and a flat distal end portion, and a head coupled to the proximal end portion of the body, wherein the second anchor includes protrusions located on an outer surface of the second anchor and below openings of the through hole, the protrusions tapered along their lengths and extending away from the outer surface of the second anchor, the protrusions arranged on the outer surface such that non-tapered areas are located between the protrusions, wherein the non-tapered areas are rounded.

2. The method of claim 1 further comprising tensioning the flexible member before placing the insertion member within the anchor cavity.

3. The method of claim 1 further comprising moving the insertion member away from the through hole, tensioning the flexible member, and moving the insertion member back toward the through hole to resecure the flexible member in the through hole.

4. The method of claim 1 wherein the protrusions create paths in a wall of the bone when the second anchor is inserted into the bone.

5. The method of claim 4 wherein the paths allow the flexible member to slide through the second anchor when the second anchor is located in the bone.

* * * * *